(12) United States Patent
Burwell et al.

(10) Patent No.: US 8,685,071 B2
(45) Date of Patent: Apr. 1, 2014

(54) MEDICAL APPARATUS EMPLOYING FLEXIBLE LIGHT STRUCTURES

(75) Inventors: Phillip Burwell, Snohomish, WA (US);
James C. Chen, Clyde Hill, WA (US);
Zihong Guo, Bellevue, WA (US);
Steven R. Daly, Sammamish, WA (US);
David B. Shine, Littleton, CO (US);
Gary Lichttenegger, Woodinville, WA (US); Jennifer K. Matson, Renton, WA (US); Jean Bishop, Issaquah, WA (US);
Nick Yeo, Horsham (GB); Hugh Narciso, Santa Barbara, CA (US)

(73) Assignee: Purdue Pharmaceutical Products L.P., Stamford, CT (US)

( * ) Notice: Subject to any disclaimer, the term of this patent is extended or adjusted under 35 U.S.C. 154(b) by 0 days.

(21) Appl. No.: 13/401,747

(22) Filed: Feb. 21, 2012

(65) Prior Publication Data

US 2012/0149986 A1 Jun. 14, 2012

Related U.S. Application Data

(60) Division of application No. 12/890,480, filed on Sep. 24, 2010, now abandoned, which is a continuation of application No. 11/323,319, filed on Dec. 30, 2005, now abandoned, which is a continuation-in-part of application No. 10/799,357, filed on Mar. 12, 2004, now Pat. No. 7,252,677.

(60) Provisional application No. 60/455,069, filed on Mar. 14, 2003, provisional application No. 60/640,382, filed on Dec. 30, 2004.

(51) Int. Cl.
*A61N 5/06* (2006.01)

(52) U.S. Cl.
USPC ............................. 607/88; 606/13; 606/15

(58) Field of Classification Search
USPC .......... 600/373–375, 377; 604/19, 20; 606/10, 606/14–17; 607/88–90, 92, 116, 129, 152
See application file for complete search history.

(56) References Cited

U.S. PATENT DOCUMENTS

| 4,445,892 A | 5/1984 | Hussein et al. |
|---|---|---|
| 4,470,407 A | 9/1984 | Hussein |

(Continued)

FOREIGN PATENT DOCUMENTS

| EP | 0755697 A2 | 1/1997 |
|---|---|---|
| MX | 2007008061 A | 7/2007 |

(Continued)

OTHER PUBLICATIONS

Nagae, T. et al. "Endovascular Photodynamic Therapy Using Mono-L-Aspartyl-Chlorin e6 to Inhibit Intimal Hyperplasia in Balloon-Injured Rabbit Arteries," *Lasers in Surgery and Medicine*, 28:381-388 (2001), Wiley-Liss, Inc.

(Continued)

*Primary Examiner* — Aaron Roane
(74) *Attorney, Agent, or Firm* — Troutman Sanders, LLP

(57) ABSTRACT

A method of manufacture and medical apparatus that provides an apparatus useful in illuminating at least a portion of a lumen of a body. The apparatus includes an elongated flexible member and a polymer encasement portion encasing a plurality of light emitters. The light emitters may be electrically coupled to one another without the use of wire bonds, and in some embodiments may be coupled without intervening electrical paths or traces. A maximum cross-sectional dimension of the polymer encasement portion may be less than twice a dimension of one of the light emitters. In some embodiments the maximum cross-sectional dimension is less than or equal to the sum of the dimension of one of the light emitters and a marginal dimension by which an outer portion of the polymer encasement portion extends beyond the light emitter. Light emitters may be arranged linearly, helically or in partially overlapping back-to-back relation.

25 Claims, 11 Drawing Sheets

(56) References Cited

U.S. PATENT DOCUMENTS

| | | |
|---|---|---|
| 5,071,407 A | 12/1991 | Termin et al. |
| 5,104,392 A | 4/1992 | Kittrell et al. |
| 5,129,889 A | 7/1992 | Hahn et al. |
| 5,330,465 A | 7/1994 | Doiron et al. |
| 5,370,608 A | 12/1994 | Sahota et al. |
| 5,445,608 A | 8/1995 | Chen et al. |
| 5,609,591 A | 3/1997 | Daikuzono |
| 5,662,712 A | 9/1997 | Pathak et al. |
| 5,766,234 A | 6/1998 | Chen et al. |
| 5,779,697 A | 7/1998 | Glowa et al. |
| 5,782,896 A | 7/1998 | Chen et al. |
| 5,800,478 A | 9/1998 | Chen et al. |
| 5,814,008 A | 9/1998 | Chen et al. |
| 5,830,210 A | 11/1998 | Rudko et al. |
| 5,941,626 A | 8/1999 | Yamuro |
| 5,947,958 A | 9/1999 | Woodard et al. |
| 5,997,571 A | 12/1999 | Farr et al. |
| 6,058,323 A | 5/2000 | Lemelson |
| 6,086,558 A | 7/2000 | Bower et al. |
| 6,171,299 B1 | 1/2001 | Bonutti |
| 6,231,568 B1 | 5/2001 | Loeb et al. |
| 6,245,012 B1 | 6/2001 | Kleshinski |
| 6,336,934 B1 | 1/2002 | Gilson et al. |
| 6,355,030 B1 | 3/2002 | Aldrich et al. |
| 6,485,502 B2 | 11/2002 | Don Michael et al. |
| 6,540,767 B1 | 4/2003 | Walak et al. |
| 6,562,058 B2 | 5/2003 | Seguin et al. |
| 6,575,965 B1 | 6/2003 | Fitch et al. |
| 6,585,655 B2 | 7/2003 | Crowley |
| 6,749,623 B1 | 6/2004 | Hsi et al. |
| 6,811,562 B1 | 11/2004 | Pless |
| 6,830,584 B1 | 12/2004 | Seguin |
| 6,953,457 B2 | 10/2005 | Farr et al. |
| 7,252,677 B2 | 8/2007 | Burwell et al. |
| 2007/0002582 A1 | 1/2007 | Burwell et al. |
| 2011/0077464 A1 | 3/2011 | Burwell et al. |

FOREIGN PATENT DOCUMENTS

| | | |
|---|---|---|
| RU | 2007128953 A | 2/2009 |
| WO | WO-0207629 A1 | 1/2002 |
| WO | WO-2004082736 A2 | 9/2004 |
| WO | WO-2006074078 A1 | 7/2006 |

OTHER PUBLICATIONS

International Searching Authority, International Search Report, counterpart PCT Application PCT/US2005/047445, mailed Apr. 25, 2006, 2 pages.

International Searching Authority, Written Opinion, counterpart PCT Application PCT/US2005/047445, Jul. 3, 2007, 6 pages.

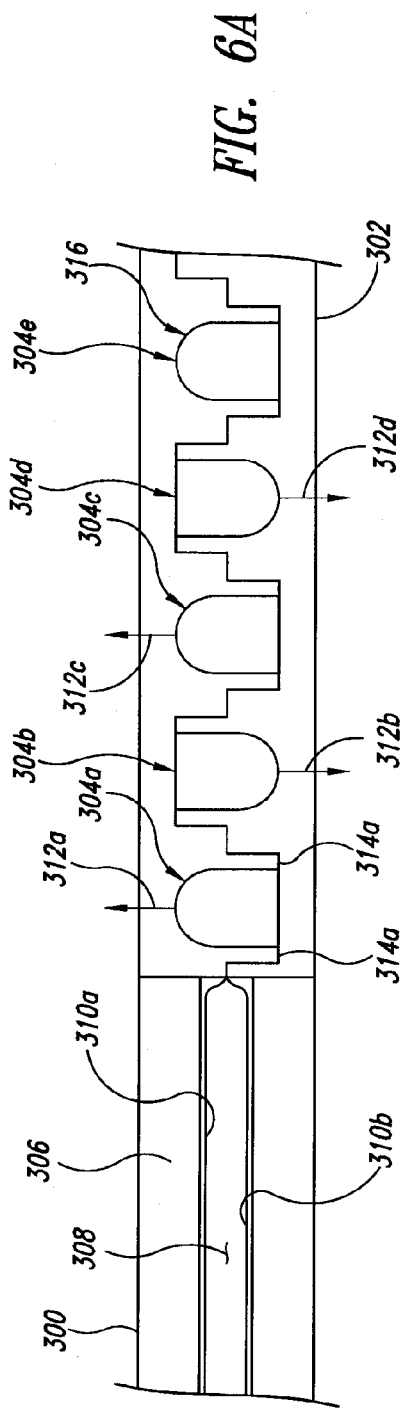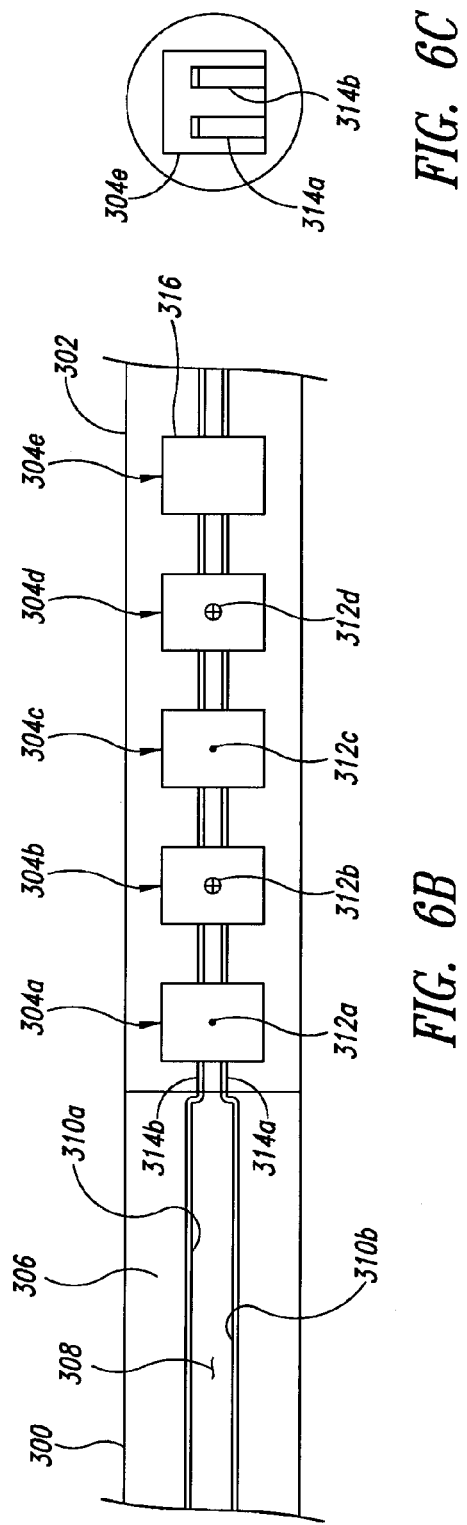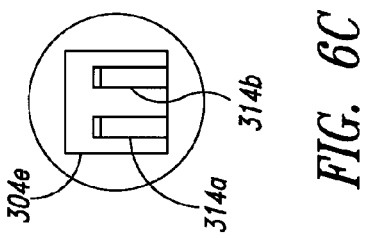

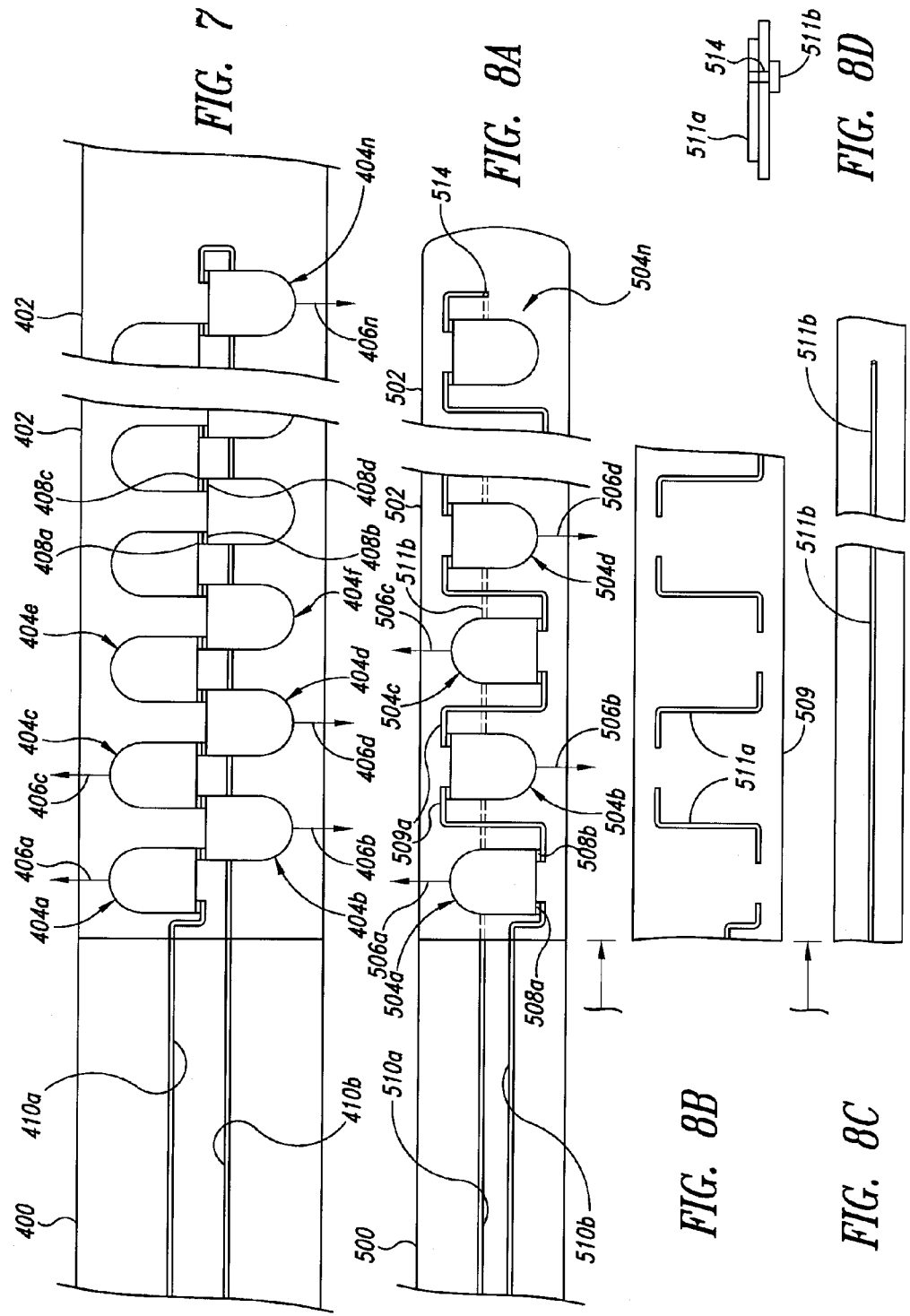

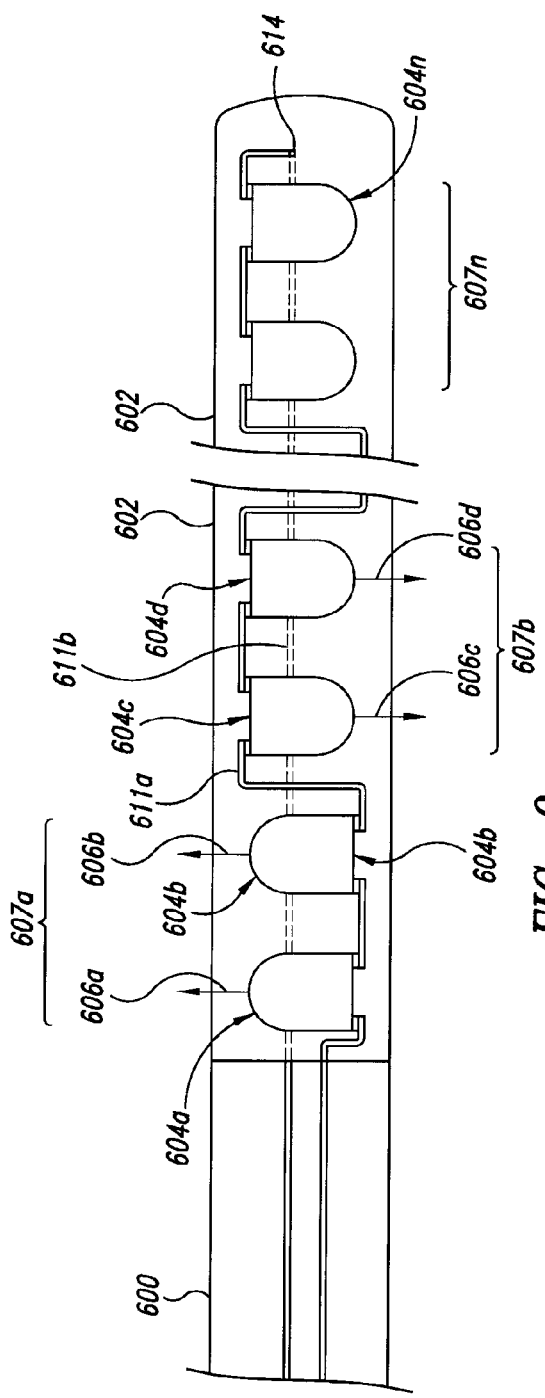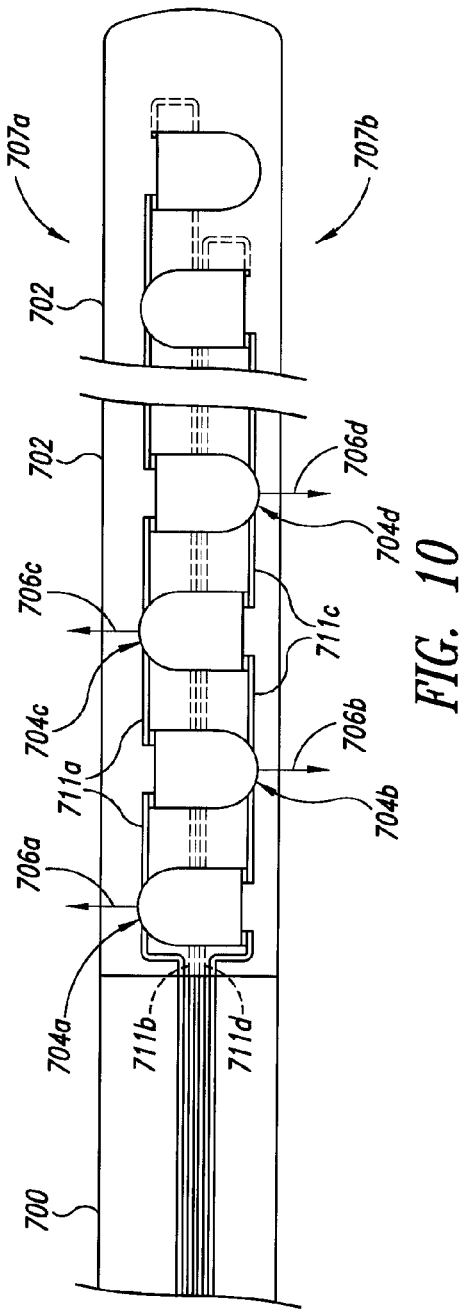

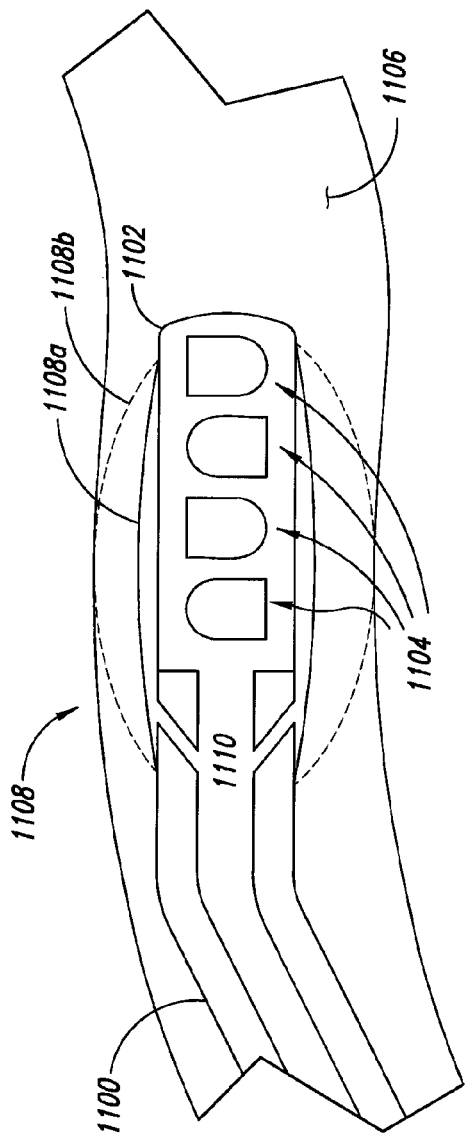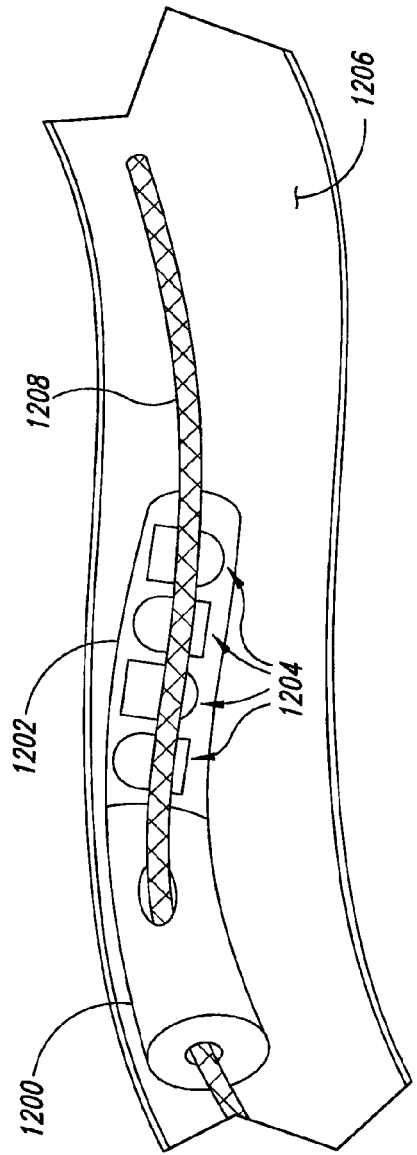

MEDICAL APPARATUS EMPLOYING FLEXIBLE LIGHT STRUCTURES

CROSS-REFERENCES TO RELATED APPLICATIONS

This application is a divisional application of U.S. patent application Ser. No. 12/890,480, filed on Sep. 24, 2010, now pending, which is a continuation of U.S. patent application Ser. No. 11/323,319, filed Dec. 30, 2005, now abandoned, which is a continuation-in-part of U.S. patent application Ser. No. 10/799,357, filed Mar. 12, 2004, which issued as U.S. Pat. No. 7,252,677 on Aug. 7, 2007, which claims the benefit under 35 U.S.C. §119(e) of U.S. Provisional Patent Application No. 60/640,382 filed Dec. 30, 2004 and U.S. Provisional Patent Application No. 60/455,069 filed Mar. 14, 2003. All of these applications are incorporated herein by reference in their entireties.

BACKGROUND OF THE INVENTION

1. Field of the Invention

The present disclosure relates to devices and methods useful in medical diagnostics and treatments, in particular diagnostics and treatments performed in a lumen of a body, for example phototherapeutic treatments that illuminate a portion of the lumen.

2. Description of the Related Art

In recent years, much research has been devoted to phototherapeutic, and especially photoreactive therapies. These therapies typically involve the excitation of a class of photoreactive compounds (i.e., "photosensitizers") that kill diseased or undesirable tissue. The photosensitizers are typically activated by illumination with at least one specific wavelength of light (i.e., excitation wavelength) and are used in photodynamic therapy (PDT). Various wavelengths may be suitable depending on the specific photosensitizer, for example wavelengths of electromagnetic radiation in the visible, infrared, and/or ultraviolet portions of the electromagnetic spectrum may be suitable.

Light sources such as lasers, emitting the appropriate excitation wavelength, are typically used to activate the photosensitizers to treat targeted tissue in a number of eye, cardiac, oncological and other disease conditions. For example, in age related macular degeneration (AMD), glaucoma, and/or diabetic retinopathy (DR), photosensitizers may be used to inhibit formation or retard disease progression such as commonly indicated by rapidly uncontrolled vascular growth (i.e., "neovascularization") within diseased eye tissue and the associated sub-retinal fluid concentration.

The two important and related components of a photoreactive treatment system are the photosensitizer and the excitation light source and apparatus for supplying the light appropriately to targeted tissue. Conventional approaches to PDT are challenged by requirements of light exposure of desired intensities, duration, shape, and timing when photosensitizers are present in the diseased tissue. Inaccurately generated illumination, such as misdirected or misshaped illumination, could have unintended affects. Accordingly, an appropriate medical apparatus for providing illumination in a lumen of a body that is well suited to the organ being treated may be a factor in successful treatment.

BRIEF SUMMARY OF THE INVENTION

Disclosed herein are medical apparatus that employ flexible devices or structures useful in treatment of human subjects with phototherapy, especially photoreactive therapy, whether intraluminal, intravascular or interstitial. These devices, each include a plurality of structures that either emit light or contain light emitters, and the structures are arranged adjacent each other to provide a compact device.

In one embodiment, a medical apparatus useful in illuminating at least a portion of a lumen of a body comprises: an elongated flexible member having a distal end and a proximal end, at least a portion of the elongated flexible member being sized and dimensioned to be received and moved within the lumen of the body; a plurality of light emitters, the light emitters electrically coupled to one another without the use of wire bonds, and operable to emit electromagnetic radiation in at least one characteristic emission waveband; and a polymer encasement portion encasing the plurality of light emitters, at least a portion of the polymer encasement portion being at least partially transmissive to electromagnetic radiation in the at least one characteristic emission waveband, and the polymer encasement portion being sized and dimensioned to be received and moved within the lumen of the body and positioned proximate the proximal end of the elongated flexible member to be moved in the lumen of the body by movement of the elongated flexible member. The light emitters have a principal axis of emission that may be oriented in two or more different directions. A maximum cross-sectional dimension of the polymer encasement portion may be less than twice a dimension of one of the light emitters measured along the principal axis of emission. The medical apparatus may include an expandable member physically coupled to move in the lumen of the body with the polymer encasement portion, and operable to expand between an expanded configuration and an unexpanded configuration. In some embodiments, the light emitters may be helically arranged.

In another embodiment, a medical apparatus useful in illuminating at least a portion of a lumen of a body comprises: an elongated flexible member having a distal end and a proximal end, at least a portion of the elongated flexible member being sized and dimensioned to be received and moved within the lumen of the body; a plurality of light emitters each having a principal axis of emission, the light emitters operable to emit electromagnetic radiation in at least one characteristic emission waveband; and a polymer encasement portion encasing the plurality of light emitters, at least a portion of the polymer encasement portion being at least partially transmissive to electromagnetic radiation in the at least one characteristic emission waveband, the polymer encasement portion having a maximum cross-sectional dimension that is less than two times the sum of a dimension of one of the light emitters measured along the principal axis of emission and a marginal dimension by which an outer portion of the polymer encasement portion extends beyond the light emitter along the principal axis of emission in a direction of principal emission, the polymer encasement portion positioned proximate the proximal end of the elongated flexible member to be moved in the lumen of the body by movement of the elongated flexible member. In some embodiments the polymer encasement portion has a maximum cross-sectional dimension that is less than or equal to the sum of the dimension of one of the light emitters measured along the principal axis of emission and the marginal dimension by which the outer portion of the polymer encasement portion extends beyond the light emitter along the principal axis of emission in the direction of principal emission. In some embodiments, the medical apparatus may include an expandable member physically coupled to move in the lumen of the body with the polymer encasement portion, at least partially transmissive to electromagnetic radiation in the at least one characteristic emission waveband, and operable to expand between an expanded configuration and an unexpanded configuration. In some embodiments, the light emitters may be helically arranged.

In another embodiment, a method of forming a medical apparatus useful in illuminating at least a portion of a lumen of a body comprises: electrically coupling a plurality of light emitters without the use of wire bonds, the light emitters operable to emit electromagnetic radiation in at least one characteristic emission waveband; encasing the plurality of light emitters in a polymer encasement portion sized and dimensioned to be received in a lumen of a body, at least a portion of the polymer encasement portion being at least partially transmissive to electromagnetic radiation in the at least one characteristic emission waveband; and physically coupling the polymer encasement portion to an elongated flexible member sized to be at least partially received in a lumen of a body. The method may further comprise helically distributing the light emitters about the longitudinal axis of the cylindrical polymer encasement portion before encasing the plurality of light emitters in a polymer encasement portion. The method may further comprise arranging the light emitters such that the polymer encasement portion has a maximum cross-sectional dimension that is less than two times the sum of a dimension of one of the light emitters measured along a principal axis of emission and a marginal dimension by which an outer portion of the polymer encasement portion extends beyond the light emitter along the principal axis of emission in a direction of principal emission, before encasing the plurality of light emitters in a polymer encasement portion. The method may further comprise arranging the light emitters such that the polymer encasement portion has a maximum cross-sectional dimension that is less than or equal to a sum of a dimension of one of the light emitters measured along a principal axis of emission and a marginal dimension by which an outer portion of the polymer encasement portion extends beyond the light emitter along the principal axis of emission in a direction of principal emission.

In yet a further embodiment, a medical apparatus useful in illuminating at least a portion of a lumen of a body comprises: an elongated flexible member having a distal end and a proximal end, at least a portion of the elongated flexible member being sized and dimensioned to be received and moved within the lumen of the body; a plurality of light emitters operable to emit electromagnetic radiation in at least one characteristic emission waveband, wherein the light emitters of the plurality of light emitters are arranged helically with respect to each other about an imaginary longitudinal axis; and a polymer encasement portion encasing the plurality of light emitters, at least a portion of the polymer encasement portion being at least partially transmissive to electromagnetic radiation in the at least one characteristic emission waveband, the polymer encasement portion positioned proximate the proximal end of the elongated flexible member to be moved in the lumen of the body by movement of the elongated flexible member.

In still a further embodiment, a method of operating a catheter physically associated with an expandable member and a plurality of light emitters to illuminate a lumen of a body comprises: inflating the expandable member with a fluid medium when the expandable member is positioned in the lumen of the body; providing power to at least some of the plurality of light emitters to provide illumination therefrom when at least some of the plurality of light emitters are positioned in the lumen of the body; and circulating the fluid medium into and out of the expandable member while the expandable member is inflated and during at least a portion of a time when the power is provided to at least some of the plurality of light emitters. Such circulation may be used to advantageously control a temperature in the lumen, for example to transfer heat generated by the light emitters away from the lumen and/or to provide heat to the lumen, for example prior to activation of the light emitters.

The light emitters may be appropriately spaced apart to allow the polymer encasement portion to flex. The light emitters may be electrically coupleable to a power source for activation either as a total array or as groups of light emitters or light emitter cases, or as individual light emitter cases. In one embodiment, the arrangement permits light to be emitted in opposite directions from the polymer encasement portion.

In each of the embodiments there are many permutations of structure arrangements possible, and many permutations of electrical activation either as single structures or as groups.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 6A is a partial cross-sectional view of an elongated flexible member and plurality of light emitters encapsulated in a flexible polymer portion, with successive ones of the light emitters in opposed relation to one another, according to one illustrated embodiment.

FIG. 6B is a partial cross-sectional view orthogonal to that of FIG. 6A.

FIG. 6C is an end view of the plurality of light emitters encapsulated in the flexible polymer portion of FIGS. 6A and 6B.

FIG. 7 is a partial cross-sectional view of an elongated flexible member and plurality of light emitters encapsulated in a flexible polymer portion, with successive ones of the light emitters in opposed overlapping relation to one another, and electrically coupled back-to-back, according to one illustrated embodiment.

FIG. 8A is a partial cross-sectional view of an elongated flexible member and plurality of light emitters encapsulated in a flexible polymer portion, with successive ones of the light emitters in opposed relation to one another, and electrically coupled in series to one another by way of a conductive path or trace carried by a flexible substrate, according to one illustrated embodiment.

FIG. 8B is a top plan view of the flexible substrate of FIG. 8A, illustrating one of the conductive paths or traces.

FIG. 8C is a bottom plan view of the flexible substrate of FIG. 8A, illustrating another one of the conductive paths or traces.

FIG. 8D is an end side view of the flexible substrate of FIGS. 8C and 8D, illustrating two of the conductive paths or traces, and a via through the substrate.

FIG. 9 is a partial cross-sectional view of an elongated flexible member and plurality of light emitters encapsulated in a flexible polymer portion, with successive sets of the light emitters in opposed relation to one another, and electrically coupled in series to one another by way of a conductive path or trace carried by a flexible substrate, according to one illustrated embodiment.

FIG. 10 is a partial cross-sectional view of an elongated flexible member and plurality of light emitters encapsulated in a flexible polymer portion, with the light emitters electrically coupled in two distinct sets which are in opposed relation to one another, the light emitters of each set electrically coupled in series to one another by way of a conductive path or trace carried by a flexible substrate, according to one illustrated embodiment.

FIG. 14 is a partial cross-sectional view of an elongated flexible member in the form of a catheter body, a plurality of light emitters encapsulated in a flexible polymer portion and an expandable member, at least partially received in a lumen of a body, according to one illustrated embodiment.

FIG. 15 is a partial cross-sectional view of a guide wire, an elongated flexible member in the form of a catheter body and a plurality of light emitters encapsulated in a flexible polymer portion, the catheter body physically coupled to the guide wire to move at least partially within a lumen of a body, according to one illustrated embodiment.

DETAILED DESCRIPTION OF THE PREFERRED EMBODIMENTS

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with light emitters, light emitting diodes, lasers, catheters, guide wires, and controllers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Figure 1:
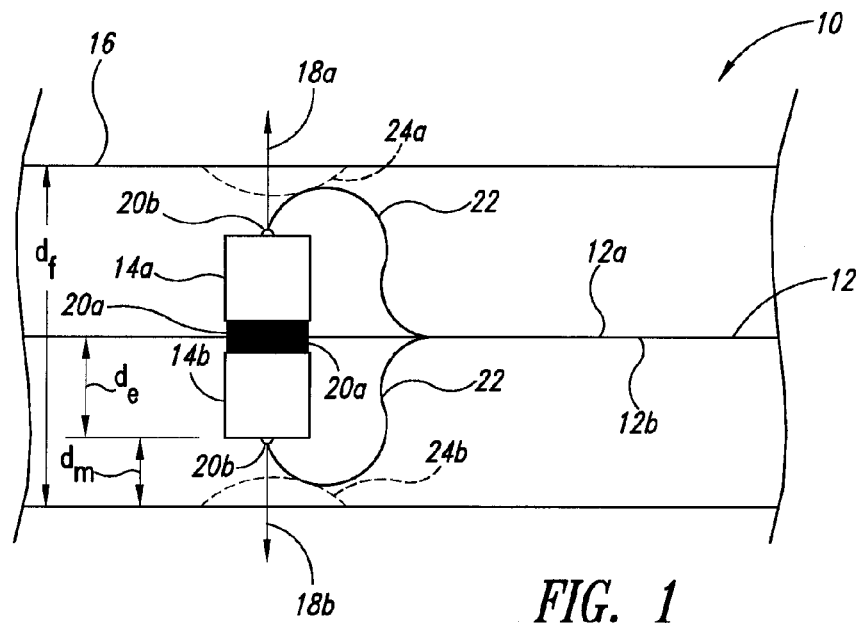
FIG. 1 is a partial side view of a conventional light emitter structure, employing a number of light emitters that are wire bonded to an electrically conductive path or trace on a flexible substrate.

FIG. 1 shows a conventional medical apparatus structure 10 for use in photoreactive therapies. The structure 10 comprises a film 12 with a pair of opposed surfaces 12a, 12b, carrying a number of light emitters 14a, 14b (collectively 14) which are encased in a protective polymer 16.

The light emitters 14 are in the form of light emitting diodes (LEDs). While each of the light emitters 14 may be capable of emitting light over a rather broad spatial range, each of the light emitters 14 has a principal axis of emission 18 about which the spatial range may be defined. The light emitters 14a, 14b are arranged in pairs, in back-to-back relationship across the film 12 with the principal axes of emission in opposed relation to provide illumination from each of the opposed surfaces 12, 12b of the film 12.

Each light emitter 14 has a pair of electrodes 20a, 20b (only one set called out in FIG. 1) that are electrically coupled to conductive paths or traces (not shown) carried by the film 12. The conductive paths or traces are usually metallic, for example copper or aluminum. One electrode 20a of each of the light emitters 14 is surface mounted to a respective conductive path or trace (not shown), while the other electrode 20b of each of the light emitters is wire bonded to a respective trace (not shown) by way of a wire bond 22 (only one called out in FIG. 1). Accordingly, power can be supplied to the light emitters 14 by way of the conductive paths or traces.

Flexing or external pressure cause mild deformation, illustrated by dashed lines 24a, 24b. As a result, the metallic wire bonds 22 and/or the coupling (e.g., solder) of the wire bond 22 with the electrode 20b of the light emitter and/or with the conductive path or trace may fail, resulting in failure of the structure 10. Additionally, the back-to-back arrangement of the light emitters 14a, 14b places constraints on the size of the structure 10. Consequently, the structure 10 has a cross-sectional dimension $d_p$ that is approximately equal to two times the sum of the dimension $d_e$ of the light emitter 14 along the principal axis of emission 18 plus the marginal thickness $d_m$ by which the polymer 16 extends beyond the light emitter 14 along the principal axis of emission 18. In this respect, it is noted that the thickness of the polymer 16 must be substantial so as to provide sufficient protection to the bonding wires 22 and attachments. This size limitation is a significant limitation in certain potential applications of the structure in photoreactive therapy.

Disclosed herein are flexible light emitter-bearing structures that are useful in photoreactive therapy, including photodynamic therapy, in intraluminal, intravascular and interstitial illumination. Some embodiments address the issue of device failure upon flexing or externally applied pressures by providing die and die wire attachment points encased in a substantially rigid, protective clear polymer. This approach permits the manufacture of devices of small cross-sectional dimensions to facilitate use in treatments where structure size is a factor. For example, the small-dimensioned structures are more suitable for invasive use within organs and blood vessels of a human body, and the dimensions facilitate use of the devices in catheters, sheaths and other lumens. A structure with a cross-sectional maximum dimension of 1.5 mm or less may be suitable for some applications. Some embodiments may permit structures with dimensions of at most 0.1 mm above the size of a single light emitter (e.g., LED) or polymer-encased light emitter, for example, 0.6 mm for a 0.5 mm encased LED. The approximately 0.1 mm difference results from the thickness of the polymer overcoating that forms the structure. This may be reduced as techniques improve. It can readily be appreciated that device dimensions may be even smaller, depending upon the size of the light emitters or encased light emitters or other light emitters used.

In some embodiments, the light emitters may take the form of light emitting diodes (LEDs), but these embodiments may employ other discrete light emitters, for example laser dies.

In each embodiment there is at least one, and preferably a plurality of structures that are light emitters or structures that contain at least one light emitter each. These structures are spaced apart from each other, and the spacing between adjacent structures may determine the degree to which a device (such as a light bar) is able to flex because flexing will cause some (reversible) deformation of the device that may result in contact between these structures depending upon the spacing distance. Thus, the selection of spacing distance should take into account the extent to which it is necessary or likely that the device will be flexed. The joined light emitters provide a linear array in a structure that forms a light bar. By the term "light bar" we mean a device that is substantially longitudinal in shape and that includes one or more light emitters at its tip and or along its length. The device is generally sized as required to be suitable for insertion into the body and/or specific organs of a human or other mammal.

While the following exemplary embodiments are described in terms of structures that are "cases" containing at least one light emitter, it is within the scope of the invention to substitute LEDs or other light emitters for the cases.

Figure 2:
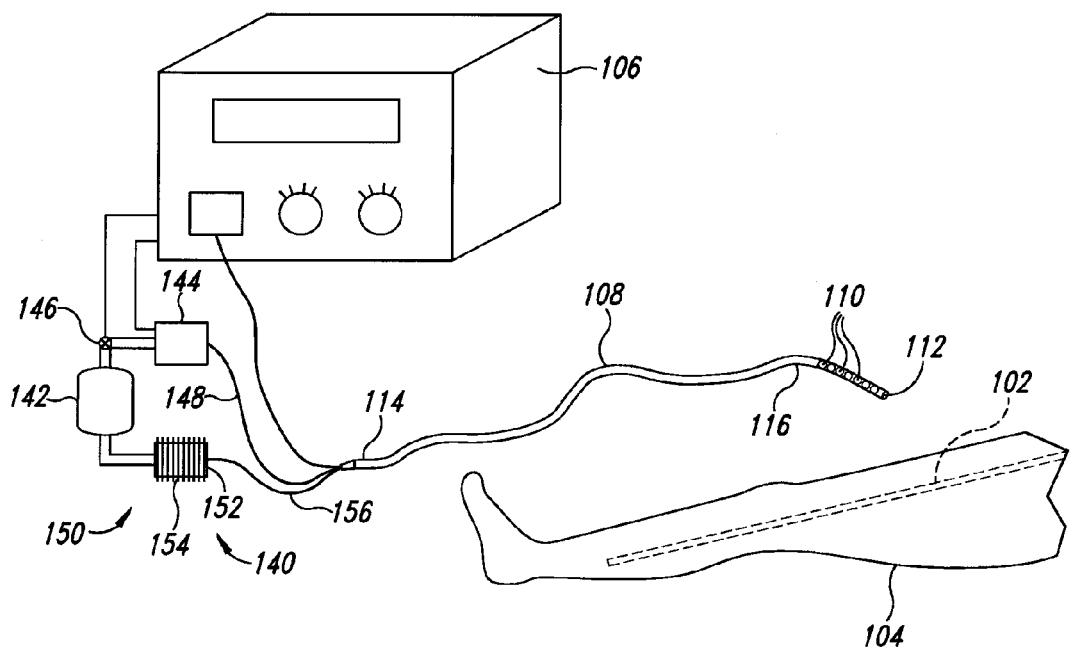
FIG. 2 is a schematic view of an environment in which a medical illumination system is employed to provide illumination in a portion of a body, according to one illustrated embodiment, the illumination system having a controller, an elongated flexible member, and a plurality of light emitters encapsulated in a flexible polymer portion.

FIG. 2 shows a medical system illumination system 100 according to one illustrated embodiment, used to provide illumination within a lumen 102 of a of a portion of a body 104. The lumen 102 may be one formed or existing in any portion of the body 104, including but not limited to blood vessels, arteries, and/or organs.

The medical illumination system comprises a controller 106, an elongated flexible member 108 and a plurality of light emitters 110 encased in a polymer encasement portion 112.

The elongated flexible member 108 has a distal end 114 and a proximate end 116, and may take a variety of forms, for example a catheter body or guide wire, and is sized and dimensioned to be at least partially received in the lumen 102 of the body 104. The polymer encasement portion 112 encasing the light emitters 110 can also take a variety of forms, for example a rod or bar, and is sized and dimensioned to be at least partially received in the lumen 102. The polymer encasement portion 112 may advantageously be one that is biocompatible or physiologically inert with respect to the body 104. The polymer encasement portion 112 may be coupled or fixed to the flexible elongated member 108 proximate the proximal end 116 thereof, or may form a unitary structure therewith.

The controller 106 provides regulated power to the light emitters 110 from a power source (not shown), for example a standard wall receptacle or a dedicated power generation device or supply, which may or may not include an auxiliary power source such as battery or fuel cell system. The controller may be physically and/or electrically coupled or fixed to the distal end of the flexible elongated member 108.

The controller 106 typically includes electrical and or electronic components to convert or transform power. For example, the controller 106 may include a rectifier to rectify alternating current to direct current, a converter to step up or step down a voltage and/or an inverter to invert direct current to alternating current. The controller 106 may advantageously provide a pulsed current to the light emitters. The controller 106 may, or may not, include user operable controls to adjust the duration, magnitude or pattern of supplied power.

The medical system illumination system 100 may optionally include a fluid circulation system 140 operable to selectively provide a fluid (i.e., gas, liquid, or vapor) to an expandable member (discussed below with reference to FIG. 14). The fluid circulation system 140 may include a storage reservoir 142 that stores the fluid and a pump 144 operable to cause transfer of the fluid between the storage reservoir 142 and the expandable member. The pump 144 may take a variety of forms including a piston pump, rotary pump, compressor, blower or fan. The controller 106 may be coupled to control the operation of the pump 144. The fluid circulation system may optionally include one or more valves 146, some or all of which may be operationally controlled by the controller 106, for example by way of one or more solenoids. One or more conduits 148 fluidly couples the storage reservoir 142 to the elongated flexible member 108.

The fluid circulation system 140 may also include a heat exchanger 150, which may include a heat exchanger reservoir 152 and heat transfer structure; for example cooling fins 154. One or more conduits 156 fluidly couples the heat exchanger 150 with the elongated flexible member 108. Some embodiments may include additional reservoirs as part of the heat exchange mechanism, or may include an active refrigeration system. Additionally or alternatively, some embodiments may include a heater to warm the fluid.

Thus the fluid circulation system 140 is operable to control a temperature proximate the polymer encasement portion 112. For example, the fluid circulation system 140 can transfer heat generated by the light emitters 110 from the polymer encasement portion 112 and lumen 102 to maintain a temperature at or close to a desired temperature. Additionally or alternatively, the fluid circulation system 140 may transfer heat to the polymer encasement portion 112 and lumen 102, for example prior to the operation of the light emitters 110 to prevent sudden changes of temperature in the lumen 102.

Figure 3:
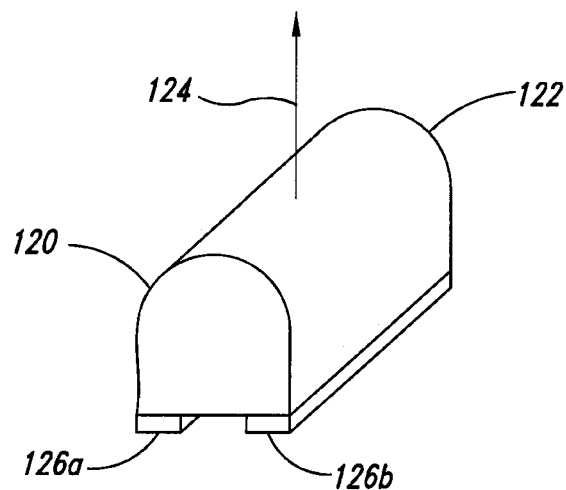
FIG. 3 is a right side, front, top isometric view of an SMT/SMD light emitter according to one illustrated embodiment.

FIG. 3 shows an SMT or SMD light emitter case 120 containing at least one LED according to one illustrated embodiment. This light emitter case 120 encapsulates the at least one light emitter device or structure, for example an LED or other light source, in a clear polymer, such as an epoxy polymer. In the illustrated embodiment, the light emitter case 120 has a top 122 that is curved like a lens, although other configurations are also useful. As noted above, while the light emitter device or structure may be capable of emitting in a broad spatial range, the light emitter case has a principal axis of emission 124 about which the spatial range is defined. Thus, while some LEDs can emit light in a 270 degree arc, there is still a principal axis of emission 124 about which the arc is defined.

The light emitter case 120 has external electrodes 126a and 126b for electrically coupling the light emitter device(s) or structure(s) to a circuit and/or power source to energize the light emitter device(s) or structure(s). There are other SMT or SMD LED and other light emitter designs that may be advantageously employed.

Figure 4:
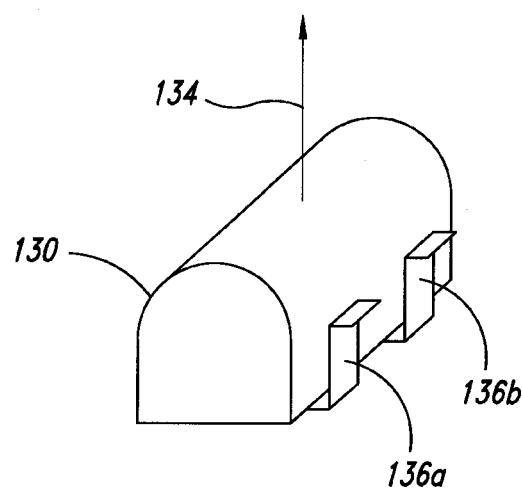
FIG. 4 is a right side, front, top isometric view of an SMT/SMD light emitter according to another illustrated embodiment.

FIGS. 3 and 4 show light emitter case 130 according to another illustrated embodiment. The light emitter case 130 encapsulates the at least one light emitter device or structure in a clear polymer. As noted above, while the light emitter device or structure may be capable of emitting in a broad spatial range, the light emitter case has a principal axis of emission 134 about which the spatial range is defined. Thus, while some LEDs can emit light in a 270 degree arc, there is still a principal axis of emission 134 about which the arc is defined.

The light emitter case 130 has external electrodes 136a, 136b for providing energizing power to the emitter(s). As explained in more detail below with reference to FIGS. 6A-6C, the electrodes 136a, 136b permit the light emitter cases 130 to be arranged in a linear array (FIG. 6) with alternating light emitter cases 130 in opposed relation relative to neighboring light emitter cases so that light is emitted in opposite directions.

FIGS. 6A-6C show an elongated flexible member 300 coupled to a polymer encasement portion 302 that encases a plurality of light emitter cases 304a-304e (collectively 304, only five illustrated) according to one illustrated embodiment.

As best illustrated in FIGS. 6A and 6B, the elongated flexible member 300 includes a wall 306 or other structure that forms a lumen or channel 308 therethrough. The lumen or channel 308 provides a passage for a conductive conduit 310a, 310b such as a conductive path or trace, or alternatively for conductive wires.

The polymer encasement portion 308 encases a plurality of light emitter cases 304. Each of the light emitter cases 304 includes at least one light emitter operable to emit electromagnetic radiation in the at least one characteristic emission waveband of the light emitters. At least a portion of the polymer encasement portion 308 proximate the light emitter cases 304 should be at least partially transmissive to electromagnetic radiation in the at least one characteristic emission waveband of the light emitters.

Figure 5:
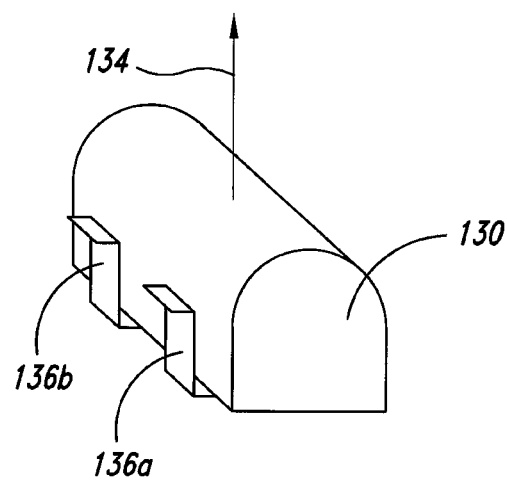
FIG. 5 is a left side, front, top isometric view of the SMT/SMD light emitter of FIG. 4.

Each of the plurality of light emitter cases 304a-304e has a respective principal axis of emission 312a-312e (collectively 312, only four illustrated). The light emitter cases 304 may advantageously take the same form as that shown in FIGS. 4 and 5, or may take other forms. The light emitter cases 304 may be joined by standard techniques (e.g., soldering, reflow soldering) or by way of an electrically conductive adhesive at the electrodes 314a, 314b (only two called out in the figure for sake of clarity of illustration), and then encased in the polymer encasement portion 316.

The light emitter cases 304 can be coupled to permit selective illumination of only certain light emitters and/or only certain groups of light emitters, if desired. In this, or any alternative, the light emitters may be electrically driven in a serial or parallel fashion along a length of the polymer encasement portion 302. The polymer encasement portion 302 may consequently have a maximum cross-sectional dimension $d_p$ that is less than two times the sum of a dimension $d_e$ of one of the light emitters 304 measured along the principal axis of emission 312 and a marginal dimension $d_m$ by which an outer portion of the polymer encasement portion 302 extends beyond the light emitter 304 along the principal axis of emission 312 in a direction of principal emission, the direction indicated by the head or tail of arrows 312. This advantageously provides a much reduced cross-sectional dimension $d_p$.

FIG. 7 shows an elongated flexible member 400 coupled to a polymer encasement portion 402 that encases a plurality of light emitter cases 404a-404n (collectively 404, twelve illustrated, seven called out in the figure) according to one illustrated embodiment. The elongated flexible member 400 is similar or identical to that discussed above in reference to FIGS. 6A-6C, so will not be described further.

Each of the light emitter cases 404 includes at least one light emitter operable to emit electromagnetic radiation in the at least one characteristic emission waveband of the light emitters. At least a portion of the polymer encasement portion 402 proximate the light emitter cases 404 should be at least partially transmissive to electromagnetic radiation in the at least one characteristic emission waveband of the light emitters.

Each of the plurality of light emitter cases 404a-404n has a respective principal axis of emission 406a-406n (collectively 406, only five illustrated and called out in the figure). The light emitter cases 404 may advantageously take the form illustrated in FIG. 3.

The light emitter cases 404 arranged in opposed, partially overlapping relation, where successively adjacent ones of the light emitter cases 404 are oriented in opposed directions such that the respective principal axes 406 are pointed in opposite directions. One electrode 408a of each light emitter case 404 is in proximate opposed relation to, or even contacts, a respective one of the electrodes 408b of a successively preceding light emitter case 404, while the other electrode 408c is in proximate opposed relation to, or even contacts one of the electrodes 408d of a successively succeeding light emitter case 404. A conductive flexible adhesive may be used to provide a series electrical connection between opposed electrodes 408a-408d of the light emitter cases 404. Electrically conductive conduits 410a, 410b, for example electrically conductive paths or traces, may provide power to the light emitter cases 404 from the controller 106 (FIG. 1).

Groups of light emitter cases 404 containing at least one light emitter device or structure each, can be electrically coupled in this manner and activated together as a group. The cross sectional-dimension $d_p$ of the polymer encasement portion 402 is at least equal to two times the sum of the a dimension $d_e$ of one of the lightemitters 304 measured along the principal axis of emission 312 and a marginal dimension $d_m$ by which an outer portion of the polymer encasement portion 402 extends beyond the light emitter 404 along the principal axis of emission 406 in a direction of principal emission.

FIGS. 8A-8D show an elongated flexible member 500 coupled to a polymer encasement portion 502 that encases a plurality of light emitter cases 504a-504n (collectively 504, five illustrated and called out in the figure) according to one illustrated embodiment. The elongated flexible member 500 is similar or identical to that discussed above in reference to FIGS. 6A-6C, so will not be described further.

Each of the light emitter cases 504 includes at least one light emitter operable to emit electromagnetic radiation in the at least one characteristic emission waveband of the light emitters. At least a portion of the polymer encasement portion 502 proximate the light emitter cases 504 should be at least partially transmissive to electromagnetic radiation in the at least one characteristic emission waveband of the light emitters.

Each of the plurality of light emitter cases 504a-504n has a respective principal axis of emission 506a-506n (collectively 506, only four illustrated and called out in the figure). The light emitter cases 504 may advantageously take the form illustrated in FIG. 3.

The light emitter cases 504 may be arranged as illustrated, such that the principal axis of emission 506 of each successive light emitter case 504b points in the opposite direction from the successively adjacent light emitter cases 504a, 504c. Alternatively the light emitter cases 504 may be arranged in groups, or may be arranged such that the principal axes 506 point in more than the two illustrated, opposed directions.

Each of the light emitter cases 504 has a pair of electrodes 508a, 508b. The electrodes 508a, 508b are electrically coupled by way of a flexible metallic or metallic-plated, shaped polymer interconnect 509, that has at least two electrical paths or traces 511a, 511b, one for each electrode 508a, 508b. A via 514 may provide an electrically conductive path from one side of the interconnect 509 to the other. Electrically conductive conduits 510a, 510b, for example electrically conductive paths or traces may provide power to the light emitter cases 404 from the controller 106 (FIG. 1).

The polymer encasement portion 302 may consequently have a maximum cross-sectional dimension $d_p$ that is less than two times the sum of a dimension $d_e$ of one of the light emitters 304 measured along the principal axis of emission 312 and a marginal dimension $d_m$ by which an outer portion of the polymer encasement portion 302 extends beyond the light emitter 304 along the principal axis of emission 312 in a direction of principal emission, the direction indicated by the head or tail of arrows 312. This advantageously provides a much reduced cross-sectional dimension $d_p$. These embodiments may be made as small in cross-sectional dimension $d_p$ as the light emitter (e.g., LED) and/or the light emitter case size permits.

This embodiment is flexible, and the electrical contacts are also flexible, unlike the prior-art wires, so that the polymer encasement portion 502 is able to flex without damage within reasonable limits in normal use.

FIG. 9 shows a flexible elongated member 600 and a polymer encasement portion 602 having light emitter cases 604 grouped into sets 604a-604n, for example sets of two 607a, 607b, 607n.

Each of the light emitter cases 604 includes at least one light emitter operable to emit electromagnetic radiation in the at least one characteristic emission waveband of the light emitters. At least a portion of the polymer encasement portion 602 proximate the light emitter cases 604 should be at least partially transmissive to electromagnetic radiation in the at least one characteristic emission waveband of the light emitters.

Principally axes of emission 606a-606d (collectively 606, only four illustrated and called out in the figure) of each light emitter case 604 in a set 407 may be aligned and point in a same direction, as illustrated. Alternatively, the principal axes of emission 606 of each light emitter case 604 may not be aligned and may not point in a same direction. The principal axes of emission 606 for successively adjacent sets 607 may point in opposite directions, as illustrated. Alternatively, the principal axes of emission 606 for a set 607 may point in the same direction as successively adjacent sets or may point in different directions.

The sets of light emitter cases 607a-607n are electrically coupled by way of at least two electrically conductive paths or traces 611a, 611b of a flexible metallic or plated polymer interconnect 609, which may include a via 614. Thus, light emitters of each set of light emitter cases may be addressed as a unit, if desired. An arrangement of this type may offer higher density packaging with a reduced number of flex points with resultant reduction in the level of overall device flexibility. Clearly, other groupings and arrangements of light emitter cases 100 along the polymer encasement portion are also possible to suit the particular needs.

FIG. 10 shows an elongated flexible member 700 coupled to a polymer encasement portion 702 that encases a plurality of light emitter cases 704a-704n (collectively 704, six illustrated and called out in the figure) according to one illustrated embodiment. The elongated flexible member 700 is similar or identical to that discussed above in reference to FIGS. 6A-6C, so will not be described further.

Each of the light emitter cases 704 includes at least one light emitter operable to emit electromagnetic radiation in the at least one characteristic emission waveband of the light emitters. At least a portion of the polymer encasement portion 702 proximate the light emitter cases 704 should be at least partially transmissive to electromagnetic radiation in the at least one characteristic emission waveband of the light emitters.

Each of the plurality of light emitter cases 704a-704n has a respective principal axis of emission 706a-706n (collectively 706, only four illustrated and called out in the figure). The light emitter cases 704 may advantageously take the form illustrated in FIG. 3.

In this embodiment, a first set of light emitter cases 707a includes every odd numbered light emitter case counting from the left to right side of FIG. 10, while a second set of light emitter cases 707b includes every even numbered light emitter case counting from the left to right side of FIG. 10. The light emitter cases of the first set 707a are electrically coupled to one another by way of at least two electrically conductive paths or traces 711a, 711b of a first flexible metallic or polymer interconnect while the light emitter cases of the second set 707b are electrically coupled to one another by way of at least two electrically conductive paths or traces, 711c, 711d of a second flexible metallic or plated polymer interconnect. The interconnect may, for example, be formed on a flexible, electrically insulative film, encased in the polymer encasement portion 702.

Figure 11B:
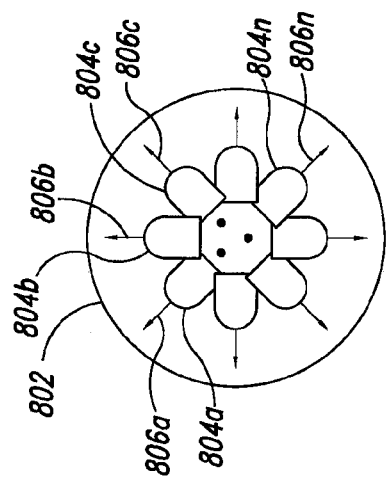
FIG. 11B is an end side view of the light emitters encapsulated in a flexible polymer portion of FIG. 11A.
Figure 11A:
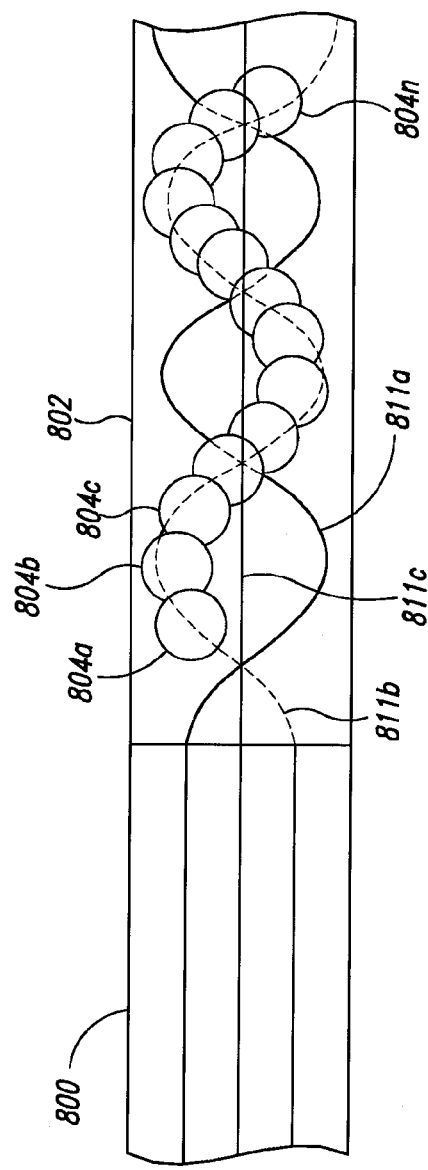
FIG. 11A is a partial cross-sectional view of an elongated flexible member and plurality of light emitters encapsulated in a flexible polymer portion, with the light emitters disposed in helical relation to one another, and electrically coupled by way of a plurality of conductive paths or traces, according to one illustrated embodiment.

FIGS. 11A and 11B show an elongated flexible member 800 coupled to a polymer encasement portion 802 that encases a plurality of light emitter cases 804a-804n (collectively 804, only four called out in the figures) according to one illustrated embodiment. The elongated flexible member 800 is similar or identical to that discussed above in reference to FIGS. 6A-6C, so will not be described further.

Each of the light emitter cases 804 includes at least one light emitter operable to emit electromagnetic radiation in the at least one characteristic emission waveband of the light emitters. At least a portion of the polymer encasement portion 802 proximate the light emitter cases 804 should be at least partially transmissive to electromagnetic radiation in the at least one characteristic emission waveband of the light emitters.

Each of the plurality of light emitter cases 804a-804n has a respective principal axis of emission 806a-806n (collectively 806, only four illustrated and called out in the figures).

The light emitter cases 804 are arranged in a helical pattern. In the illustrated embodiment, the respective principal axes of emission 806 point outward from the polymer encasement portion 802 in a plurality of directions, and may be arranged to provide relatively even illumination in 360 degrees.

The light emitter cases are electrically coupled to a number of electrically conductive paths or traces 811a-811c of helical metallic or helical molded metallized polymer interconnects. It is appreciated that the polymer encasement structure 802 may employ a greater or lesser number of light emitter cases 804, and that such light emitter cases 804 may be distributed in a variety of ways to provide emitted light from all around the polymer encasement portion 802.

Figure 12:
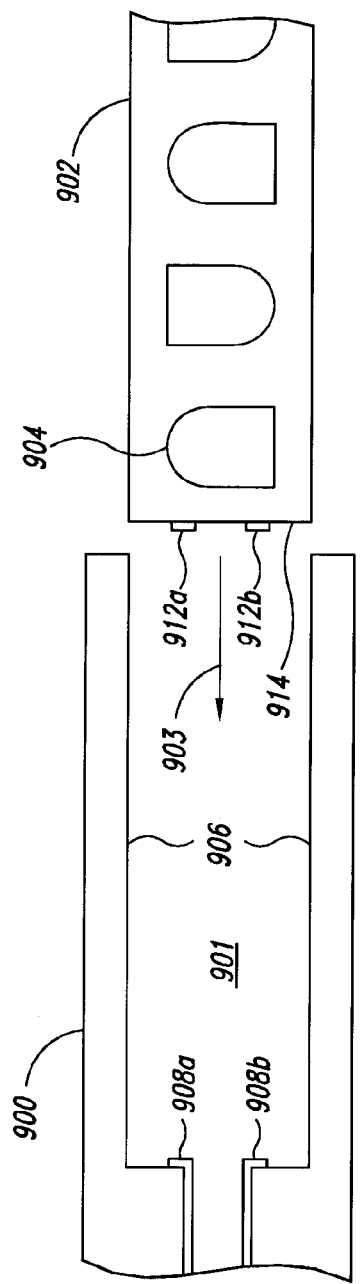
FIG. 12 is a partial cross-sectional view of an elongated flexible member having a receptacle sized to at least partially receive the plurality of light emitters encapsulated in a flexible polymer portion, according to one illustrated embodiment.

FIG. 12 shows an elongated flexible member 900 that forms a receptacle 901 sized and dimensioned to at least partially receive a polymer encasement portion 902 as indicated by arrow 903, according to one illustrated embodiment.

The polymer encasement portion 902 encases a plurality of light emitter cases 904. At least a portion 906 of the elongated flexible member 900 proximate the receptacle 901 should be at least partially transmissive to electromagnetic radiation in the at least one characteristic emission waveband of the light emitters. Contacts 908a, 908b, may be formed at a bottom 910 of the receptacle 901 and complimentary contacts 912a, 912b formed on a bottom 914 of the polymer encasement portion 902 to provide a conductive electrical path upon insertion and seating of the polymer encasement portion 902 into the receptacle. The elongated flexible member 900 may include mechanical engagement structure(s) to ensure proper seating and/or retention of the polymer encasement portion 902 in the receptacle 901.

Figure 13:
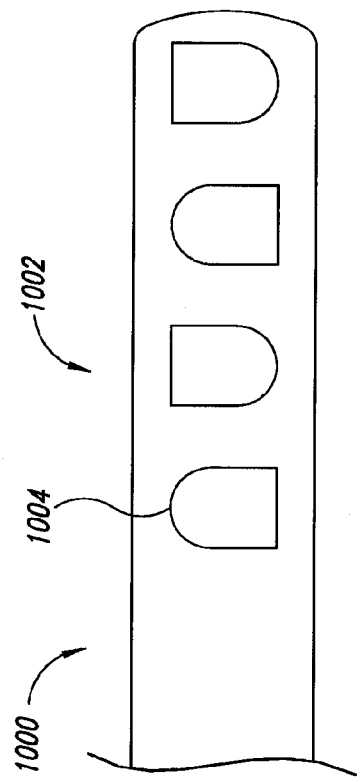
FIG. 13 is a partial cross-sectional view of a unitary structure having an elongated flexible member and plurality of light emitters encapsulated in a flexible polymer portion, according to one illustrated embodiment.

FIG. 13 shows a unitary structure that forms an elongated flexible member 1000 and a polymer encasement portion 1002 encasing a plurality of light emitter cases 1004, according to one illustrated embodiment. The elongated flexible member 1000 may advantageously be a polymer and cast, extruded, or otherwise formed along with the polymer encasement portion 1002 as a single unitary piece. At least a portion of the polymer encasement portion 1002 proximate the light emitter cases 1004 should be at least partially transmissive to electromagnetic radiation in the at least one characteristic emission waveband of the light emitters.

FIG. 14 shows an elongated flexible member in the form of a catheter body 1100 and a polymer encasement portion 1102 encasing a plurality of light emitters 1104 received in a lumen 1106 of a body according to one illustrated embodiment.

An expandable member 1108, for example a balloon, may be selectively expanded between an unexpanded configuration (shown in solid line 1108a) and an expanded configuration (shown in broken line 1108b) to engage the wall forming the lumen 1106. The catheter body 1100 may include one or more lumens or channels 1110 to transfer a fluid (e.g., liquid or gas) between the expandable member 1108 and one or more reservoirs (not shown). In some embodiments the fluid may be recirculated to transfer heat generated by the light emitters 1104 away from the lumen 1106 of the body.

The expandable member 1108 may be positioned overlying or surrounding the light emitters 1104 as illustrated, in which case at least a portion of the expandable member 1108 should be at least partially transmissive to electromagnetic radiation in the at least one characteristic emission waveband of the light emitters 1104. In other embodiments the expandable member 1108 may be positioned so as to not overlie or surround the light emitters 1104.

Some embodiment may include two, or more, expandable members. For example, some embodiments may include two expandable members located fore and aft of the light emitters. In such an embodiment, a first one of the expandable members may be expanded to stop the flow of a bodily fluid (e.g., blood), then the second one of the expandable members expanded after a portion of the lumen 1106 has cleared of the bodily fluid. This may advantageously allow the lumen 1106 of the body to be illuminated without the interference of the bodily fluid.

FIG. 15 shows an elongated flexible member in the form of a catheter body 1200 and a polymer encasement portion 1202 encasing a plurality of light emitters 1204, all received in a lumen 1206 of a body according to one illustrated embodiment. The catheter body 1200 is coupled to move along a guide wire 1208, which may be inserted into the lumen 1206 prior to insertion of the catheter body 1200 and polymer encasement portion 1202.

Figure 16:
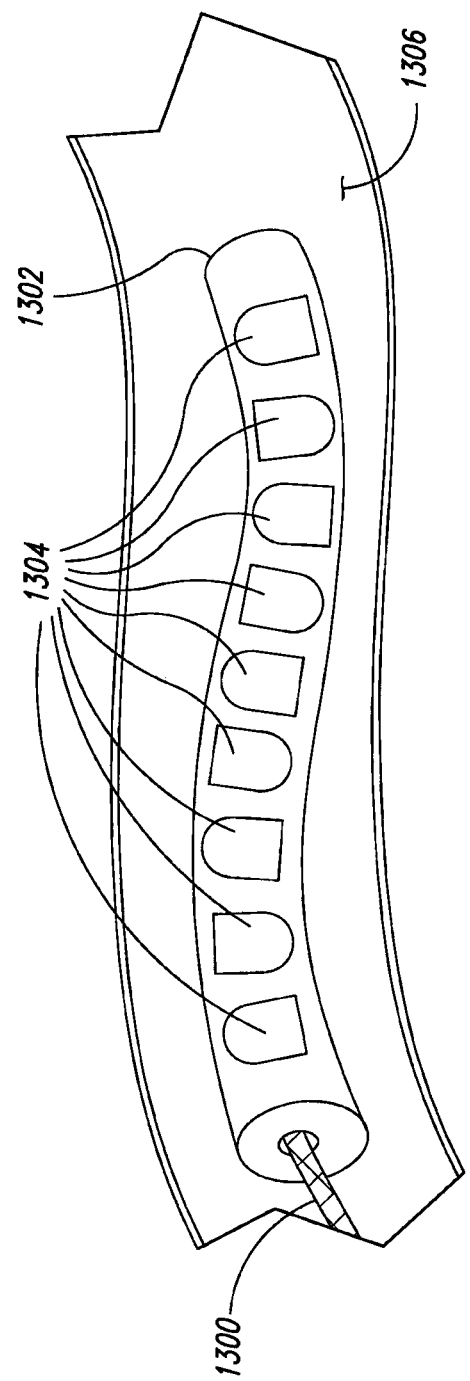
FIG. 16 is a partial cross-sectional view of a guide wire, an elongated flexible member in the form of a guide wire and a plurality of light emitters encapsulated in a flexible polymer portion physically coupled to the guide wire to move at least partially within a lumen of a body, according to one illustrated embodiment.

FIG. 16 shows an elongated flexible member in the form of a guide wire 1300 and a polymer encasement portion 1302 encasing a plurality of light emitters 1304, all received in a lumen 1306 of a body according to one illustrated embodiment. While the figure illustrates the polymer encasement portion 1302 attached or fixed to the guide wire 1300, in other embodiments the polymer encasement portion 1302 may be slideably or otherwise movably mounted to the guide wire 1300.

Figure 17:
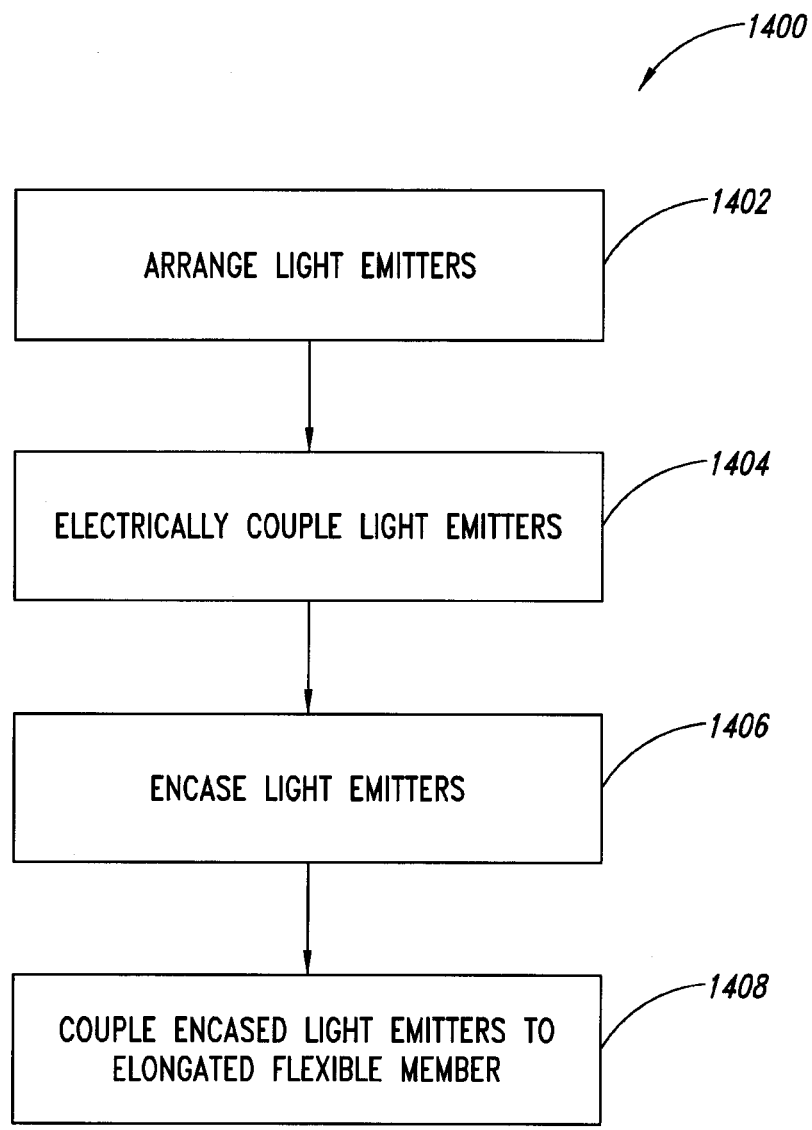
FIG. 17 is flow diagram showing a method of forming a medical device having an elongated flexible member and a plurality of light emitters encapsulated in a flexible polymer portion, according to one illustrated embodiment.

FIG. 17 shows a method 1400 of manufacturing a medical apparatus according to one illustrated embodiment.

At 1402, the light emitters are arranged in a desired topology. As described above, the light emitters may be arranged in a variety of topologies, for example linear array, or helically disposed. The light emitters may be arranged with principal axes of emission all pointing in a common direction, or in opposed directions or in three or more directions. The light emitters may be arranged in partial overlapping back-to-back relation. The light emitter may be arranged in groups with principal axes of emission of the light emitters of any group pointing in a common direction, and groups pointing in different directions. Alternatively, the light emitter may be arranged in groups with principal axes of emission of the light emitters of any group pointing in a variety of directions.

At 1404, the light emitters are electrically coupled. As described above, the light emitters may be coupled to one another without the use of wire bonds. Further, the light emitters may be coupled to one another without the use of electrically conductive paths or traces, for example when arranged in back-to-back partially overlapping relation or where arranged such that the terminals of neighboring light emitters are proximate or in contact with one another. Alternatively, the light emitters may be coupled to one another using electrically conductive paths or traces, for example those of a flexible interconnect.

At 1406, the light emitters are encased in the polymer encasement portion. The encasement may advantageously fix the topology of the light emitters, as well as provide environmental protection.

Optionally at 1408, the encased light emitters are electrically coupled to the elongated flexible member. Such coupling may be completed during manufacture, or may be completed by an end user, for example just prior to use. Such may allow a portion (e.g., catheter body, wire guide or polymer encasement portion) of the device to be sterilized and reused, or may allow the selection of a particular component based on the subject, patient, disease or procedure. In some embodiments, the elongated flexible member and polymer encasement portion are formed as a unitary structure, thus the electrical coupling may already exist.

Figure 18:
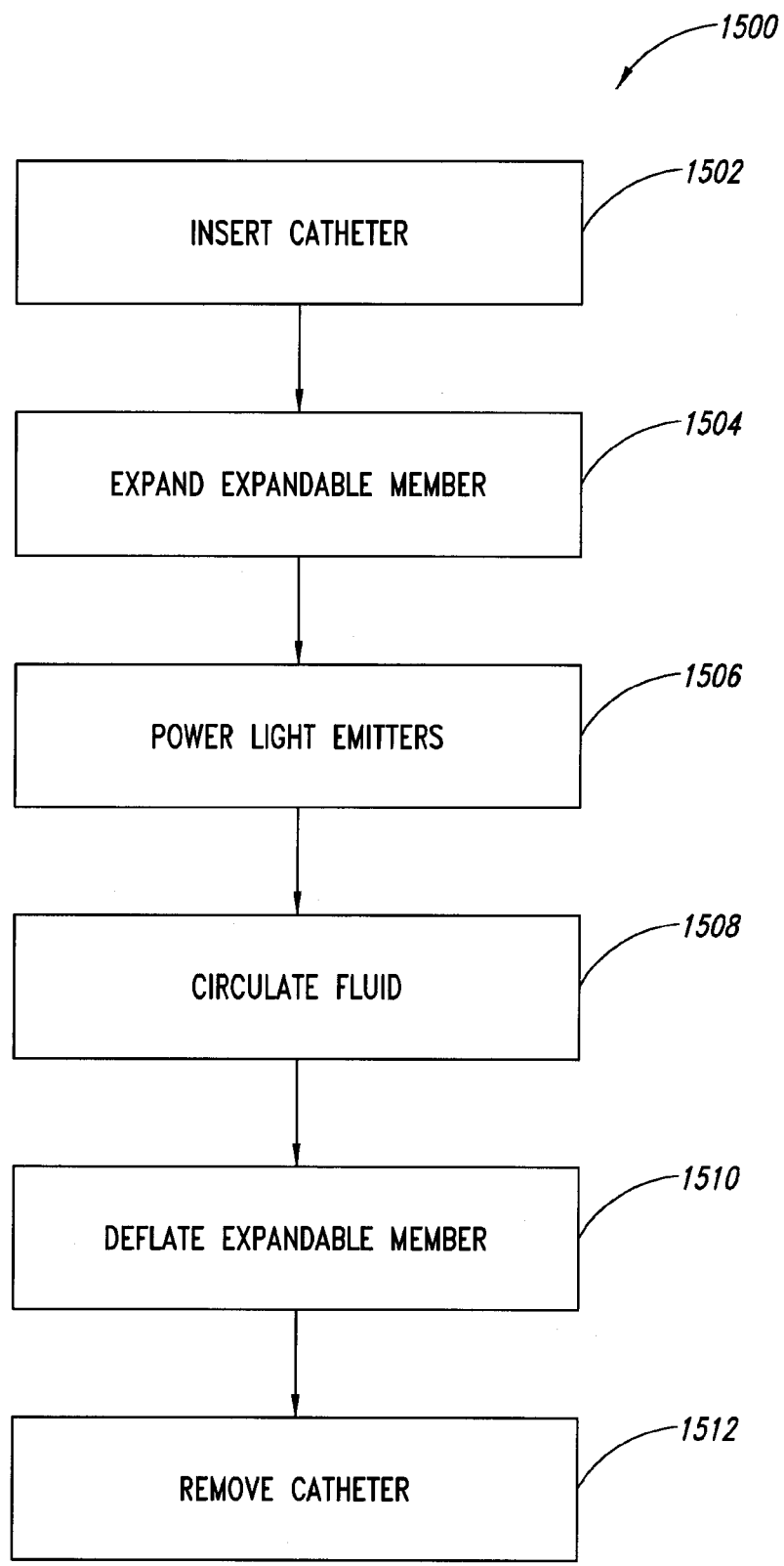
FIG. 18 is a flow diagram showing a method of using a medical illumination system including circulating a fluid through an expandable member to control a temperature, according to one illustrated embodiment.

FIG. 18 shows a method 1500 of using a medical system illumination system 100 including a fluid circulation system 140 (FIG. 2) according to one illustrated embodiment.

At 1502, at least a portion of the catheter having the expandable member is inserted into the lumen 102 (FIG. 2) of the body. The catheter body and/or guide wire is used to maneuver the polymer encasement portion 112 Proximate an area of the lumen 102 to be illuminated.

At 1504, the fluid circulation system 140 expands the expandable member 1108 (FIG. 14), for example inflating the expandable member 1108 with a fluid medium using the storage reservoir 142 and pump 144 (FIG. 2). As noted above, some embodiments may include more than one expandable member. Such embodiments may employ additional storage reservoirs, pumps and/or conduits for inflating or otherwise actuating the respective expandable members.

At 1506, the controller provides power to at least some of the plurality of light emitters to illuminate at least a portion of the lumen 102 of the body. As discussed above, the controller 106 can cause a variety of spatial or temporal patterns of illumination, and can vary or otherwise control intensity of illumination.

At 1508, the fluid circulation system 140 circulates the fluid medium into and out of the expandable member 1108 while the expandable member 1108 is inflated and during at least a portion of a time when the power is provided to at least some of the plurality of light emitters. Heat generated by the light emitters may be transferred to the fluid in the expandable member 1108, and then transferred away from the lumen 102 to the heat exchanger 150 (FIG. 2). Alternatively, or additionally, heat may be supplied to the expandable member 1108 by way of the fluid to warm the lumen prior to and/or following operation of the light emitters.

At 1510, the expandable member 1108 is at least partially deflated. At 1512, the catheter is then removed from the lumen 102.

The above description of illustrated embodiments, including what is described in the Abstract, is not intended to be exhaustive or to limit the claims invention to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein can be applied to various medical devices, not necessarily the exemplary catheter type medical device for photodynamic therapy generally described above.

For example, in the area of oncology, PDT may potentially be used to treat and kill diseased cells, such as cancer cells, without substantial injury to surrounding healthy tissue. A polymer encasement portion may contain as many light emitter cases as necessary or useful for the particular application, and the light emitter cases may be grouped in any manner necessary or useful for the intended application.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to commonly assigned U.S. provisional patent application Ser. No. 60/640,382, filed Dec. 30, 2004; commonly assigned U.S. provisional patent application Ser. No. 60/455,069 filed Mar. 14, 2003; and commonly assigned U.S. nonprovisional patent application Ser. No. 10/799,357, filed Mar. 12, 2004; are incorporated herein by reference, in their entirety. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all medical apparatus that operate in accordance with the claims. Accordingly, the invention is not limited by the disclosure, but instead its scope is to be determined entirely by the following claims.

The invention claimed is:

1. A catheter for illuminating at least a portion of a lumen of a subject, comprising:
  a flexible light bar including
    a plurality of light emitters, and
    a plurality of electrical connections, each electrical connection having a first end electrically connected to one of the light emitters, a second end opposing the first end and electrically connected to another one of the light emitters, and at least one S-shaped portion between the first end and the second end; and
  a cylindrical polymer encasement portion having a maximum cross-sectional diameter that is less than about 1.5 mm,
  wherein the polymer encasement portion completely encases the plurality of light emitters and the electrical connections,
  wherein the at least one S-shaped portion of the electrical connections provides an offset arrangement for adjacent light emitters such that the adjacent light emitters overlap when viewed along a longitudinal axis of the polymer encasement portion to reduce a diameter of the polymer encasement portion,
  wherein the longitudinal axis of the polymer encasement portion intersects at least a portion of each adjacent light emitter;
  wherein the electrical connections connect the light emitters without the use of a planar mounting strip extending along most of a length of the light bar such that only the polymer encasement portion and the electrical connections mechanically couple the plurality of light emitters together.

2. The catheter of claim 1 wherein each of the electrical connections includes a pair of S-shaped portions.

3. The catheter of claim 1 wherein the plurality of light emitters are at different orientations relative to one another to deliver light from opposing longitudinal sides of the polymer encasement portion.

4. The catheter of claim 1 wherein the electrical connections extend between and electrically connect terminals of adjacent light emitters.

5. The catheter of claim 1, further comprising a distal tip consisting essentially of the plurality of light emitters, the plurality of electrical connections, and the polymer encasement portion.

6. A catheter, comprising:
  an elongated flexible member having a distal end and a proximal end, at least a portion of the elongated flexible member being sized and dimensioned to be received and moved within a lumen of a body;
  a light bar including a plurality of light emitters being operable to emit electromagnetic radiation in at least one characteristic emission waveband, the light emitters electrically coupled to one another by electrical connections without the use of a flat mounting substrate strip that both carries the electrical connections and that extends along most of a longitudinal length of the light bar; and a cylindrical encasement portion completely encases the light bar and being coupled to the elongated flexible member, at least a portion of the cylindrical encasement portion being at least partially transmissive to electromagnetic radiation in the at least one characteristic emission waveband, and the cylindrical encasement portion being sized and dimensioned to be received and moved along the lumen of the body, wherein the electrical connections provide an offset arrangement for adjacent light emitters such that the adjacent light emitters overlap when viewed along a longitudinal axis of the cylindrical encasement portion to reduce a diameter of the cylindrical encasement portion, wherein the longitudinal axis of the cylindrical encasement portion intersects at least a portion of each of the light emitters.

7. The catheter of claim 6 wherein each of the plurality of light emitters has a principal axis of emission.

8. The catheter of claim 7 wherein the principal axis of emission of a first one of the plurality of light emitters is in a different direction than the principal axis of emission of another one of the plurality of light emitters.

9. The catheter of claim 6 wherein a maximum cross-sectional diameter of the encasement portion is less than about 1.5 mm.

10. The catheter of claim 6 wherein the plurality of light emitters are arranged to provide circumferential illumination.

11. The catheter of claim 6 wherein a principal axis of emission of at least some of the light emitters is diametrically opposed to a principal axis of emission of successively adjacent ones of the light emitters.

12. The catheter of claim 6 wherein the electrical connections have a substantially S-shaped configuration.

13. The catheter of claim 6 wherein the encasement portion is substantially cylindrical with a longitudinal axis.

14. The catheter of claim 6 wherein only the encasement portion and electrical connections mechanically couple the light emitters together.

15. The catheter of claim 6 wherein the encasement portion comprises a transparent polymer cylinder.

16. The catheter of claim 6 wherein the encasement portion physically contacts a substantial portion of each external face of the light emitters.

17. A medical apparatus for illuminating at least a portion of a lumen of a body of an individual, the medical apparatus comprising:

a cylindrical encasement portion; and a light bar completely encased in the cylindrical encasement portion, the light bar including a plurality of light emitters and a plurality of electrical connections, the plurality of light emitters being electrically coupled together without the use of a planar mounting strip extending along most of a length of the light bar, the light emitters having at least two terminals, each electrical connection having a first end and a second end, the first end of the electrical connection being directly connected to a respective terminal of one of the light emitters and the second end of the electrical connection being directly connected to one of the terminals of another one of the light emitters such that adjacent light emitters are in a offset arrangement in which adjacent light emitters point in different directions and adjacent light emitters overlap when viewed along a longitudinal axis of the cylindrical encasement portion, wherein the longitudinal axis intersects at least a portion of the adjacent light emitters; and wherein the cylindrical encasement portion completely encases the light bar and structurally supports the light emitters.

18. The medical apparatus of claim 17 wherein at least two of the light emitters each have a top portion and a bottom portion, the bottom portion includes a bottom face and two terminals, and two of the electrical connections are S-shaped, directly connected to the two terminals of the bottom portion and encapsulated by the encasement portion.

19. The medical apparatus of claim 17 wherein most of a longitudinal length of at least one of the electrical connections is between a pair of the light emitters.

20. A medical apparatus for placement in a lumen of a body, the medical apparatus comprising:

a cylindrical an elongate main body configured to be moved through the lumen of the body;

a light bar including a plurality of light emitting devices completely encapsulated by the elongate main body and operable to receive electrical energy and to produce electromagnetic radiation that passes through the elongate main body; and a plurality of electrical connections that connect the light emitting devices without the use of a planar mounting strip extending along most of the length of light bar, wherein one of the electrical connections has a first end directly connected to a first one of the light emitting devices, a second end directly connected to a second one of the light emitting devices, wherein the first one of the light emitting devices is adjacent to the second one of the light emitting devices, and the elongate main body encases both the first one of the light emitting devices and the second one of the light emitting devices, wherein the electrical connections provide an offset arrangement of adjacent light emitting devices such that the adjacent light emitting devices point in different directions and the light emitting devices overlap when viewed along a longitudinal axis of the elongate main body to reduce the diameter of the elongate main body, wherein the longitudinal axis of the elongate main body intersects at least portions of the light emitting devices.

21. The medical apparatus of claim 20 wherein a main body of one of the electrical connections extends between the first end and the second end, and the entire main body of the electrical connection is encapsulated by the elongate main body.

22. The medical apparatus of claim 20 wherein the elongate main body is made of a transparent material that encapsulates all of the light emitting devices.

23. The medical apparatus of claim 20, further comprising a plurality of S-shaped electrical connections spaced apart from one another with respect to a longitudinal axis of the elongate main body, respective S-shaped electrical connections being positioned between respective pairs of the light emitters with most of a longitudinal length of the respective S-shaped electrical connections being positioned between the respective pair of light emitters.

24. The medical apparatus of claim 20 wherein at least one of the light emitting devices is positioned to output light from a first side of the elongate main body and another one of the light emitting devices is positioned to output light from a second side of the elongate main body, the first side being substantially diametrically opposed to the second side.

25. The medical apparatus of claim 20 wherein the light emitting devices comprise light emitter cases containing at least one light emitter.

\* \* \* \* \*